United States Patent
Fitzgerald et al.

(10) Patent No.: US 8,257,420 B2
(45) Date of Patent: Sep. 4, 2012

(54) STENT DELIVERY CATHETER SYSTEM WITH HIGH TENSILE STRENGTH

(75) Inventors: Keif Fitzgerald, San Jose, CA (US); Leticia Castillon, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 611 days.

(21) Appl. No.: 12/271,053

(22) Filed: Nov. 14, 2008

(65) Prior Publication Data
US 2010/0125322 A1    May 20, 2010

(51) Int. Cl.
*A61F 2/06* (2006.01)
(52) U.S. Cl. ...................................... 623/1.11
(58) Field of Classification Search ............ 623/1.11, 623/1.12; 606/108; 604/523–539; 600/139
See application file for complete search history.

(56) References Cited

U.S. PATENT DOCUMENTS

| | | | | |
|---|---|---|---|---|
| 5,176,660 A | * | 1/1993 | Truckai | 604/527 |
| 5,222,969 A | * | 6/1993 | Gillis | 606/194 |
| 5,421,826 A | * | 6/1995 | Crocker et al. | 604/509 |
| 5,429,597 A | | 7/1995 | DeMello et al. | |
| 5,507,768 A | * | 4/1996 | Lau et al. | 623/1.11 |
| 5,571,087 A | | 11/1996 | Ressemann et al. | |
| 5,772,668 A | * | 6/1998 | Summers et al. | 623/1.11 |
| 5,827,242 A | * | 10/1998 | Follmer et al. | 604/526 |
| 5,843,092 A | * | 12/1998 | Heller et al. | 606/108 |
| 6,149,574 A | * | 11/2000 | Trauthen et al. | 600/3 |
| 6,368,344 B1 | * | 4/2002 | Fitz | 623/1.11 |
| 6,613,075 B1 | | 9/2003 | Healy et al. | |
| 6,679,909 B2 | * | 1/2004 | McIntosh et al. | 623/1.11 |
| 6,695,862 B2 | | 2/2004 | Cox et al. | |
| 6,989,024 B2 | | 1/2006 | Hebert et al. | |
| 7,001,420 B2 | * | 2/2006 | Speck et al. | 623/1.11 |
| 7,905,877 B1 | * | 3/2011 | Jimenez et al. | 604/525 |
| 2008/0039863 A1 | * | 2/2008 | Keegan et al. | 606/108 |

* cited by examiner

*Primary Examiner* — Gary Jackson
*Assistant Examiner* — Amy Shipley
(74) *Attorney, Agent, or Firm* — Fulwider Patton LLP

(57) ABSTRACT

A stent delivery catheter system having a reinforcing tether member secured to the catheter such that the catheter is provided with an improved combination of an enhanced tensile strength together with other catheter performance characteristics such as low profile and high flexibility. The stent delivery system includes an elongated delivery catheter including a reinforcing tether member secured to the inner tubular member of the catheter. The tether member has a distal end length extending helically from the distal tip member or proximally adjacent to the proximal end of the distal tip member of the catheter and a portion that also extends axially through the stent holder region of the catheter. This reinforcing tether member provides enhanced tensile strength to the catheter.

24 Claims, 3 Drawing Sheets

STENT DELIVERY CATHETER SYSTEM WITH HIGH TENSILE STRENGTH

BACKGROUND OF THE INVENTION

This invention relates generally to catheters, and more particularly to catheter systems for percutaneous transluminal procedures, such as delivery and deployment of expandable prostheses.

In the treatment of vascular and biliary disease, expandable endoprosthesis devices, generally called stents, are commonly implanted into a patient's body lumen to maintain the patency thereof. Stents are particularly useful in the treatment and repair of body lumens after a stenosis has been compressed by percutaneous transluminal coronary angioplasty (PTCA) or percutaneous transluminal angioplasty (PTA), or removed by atherectomy or other means, to help improve the results of the procedure and reduce the possibility of restenosis. Stents are generally cylindrically shaped devices which function to hold open a segment of a blood vessel such as a coronary artery, or other body lumen such as a bile duct. Stents are usually delivered in a collapsed state on a catheter to the target site and then deployed at that location by expanding to a larger diameter into contact with the body lumen wall. Stents are generally classified into one of two categories related to the expansion of the stent, namely, stents which require application of a radially outward force such as by inflating a catheter balloon on which the stent is mounted, or alternatively, self-expanding stents which will automatically expand from the collapsed state when the stent is advanced out the distal end of a radial restraining member of the delivery catheter.

Prior art stent delivery systems for implanting self-expanding stents typically include an inner lumen around which the collapsed stent is positioned and an outer restraining sheath which is initially placed over the collapsed stent prior to deployment. When the stent is to be deployed in the body vessel, the outer sheath is moved in relation to the inner lumen to uncover the collapsed stent, allowing the stent to expand to its expanded condition. Delivery systems have utilized a push-pull type technique in which the outer sheath is retracted while the inner lumen is pushed forward, or have been designed to retract the outer sheath and deploy the stent while the inner lumen must remain stationary to prevent the stent from moving axially within the body lumen during deployment.

In certain applications, the stent delivery catheter is required to have a relatively low profile to facilitate positioning the operative distal end portion of the catheter at the desired treatment site in the patient's body lumen. However, catheter profile must be balanced with competing considerations such as the catheter tensile strength and kink resistance, and other important characteristics such as those related to the nature of the materials used to form the catheter components. For example, a catheter with a distal shaft section having a large wall thickness likely has sufficient catheter tensile strength but insufficient flexibility and low profile or lumen size to be practicable in all applications. A catheter design having insufficient tensile strength can result a catheter failure as the catheter is under tension while being proximally retracted from within the patient's body lumen, such that the catheter shaft partially or completely tears, which can result in the potentially lethal dislocation of the catheter distal tip. Therefore, what has been needed is a stent delivery catheter system with an improved balance of these catheter characteristics. The present invention satisfies these and other needs.

SUMMARY OF THE INVENTION

The present invention is directed to a stent delivery catheter system having a reinforcing tether member secured to the catheter, such that the catheter is provided with an improved combination of an enhanced tensile strength together with other catheter performance characteristics such as low profile and high flexibility.

In one embodiment, a stent delivery catheter system of the invention generally includes an elongated delivery catheter having an inner tubular member, a stent holder region, a guidewire lumen-defining tubular member extending within at least a distal section of the inner tubular member and within the stent holder region, a distal tip at a distal end of the guidewire lumen-defining tubular member, an outer tubular member which has a stent restraining region and which is adapted for axial movement with respect to the inner tubular member to transition from an advanced configuration surrounding the stent holder region to a proximally retracted configuration, and a reinforcing tether member extending along the guidewire-defining tubular member. The reinforcing tether member is typically secured to the distal tip member and the inner tubular member. A self-expanding stent in a collapsed configuration surrounds the stent holder region and is radially restrained by the advanced catheter outer tubular member. The stent is configured to be deployed by radially self-expanding from the collapsed configuration upon movement of the catheter outer tubular member to the retracted configuration, to thereby release the radial restraining force of the outer tubular member. The reinforcing tether member is configured to enhance the tensile strength of the catheter. In one embodiment, the reinforcing tether member extends at least in part helically in the distal tip, and extends proximally from the proximal end of the distal tip member on the guidewire-defining tubular member in an axial manner (i.e., aligned with the longitudinal axis of the catheter). In an alternative embodiment, the reinforcing tether member distal end is located at the proximal end of the distal tip such that it extends at least in part helically proximally adjacent to the proximal end of the distal tip member on the guidewire lumen-defining tubular member. The reinforcing tether member is typically a metallic round wire, although it could alternatively be a flat ribbon or other high tensile fiber, and may be a single or multi-fiber strand, and a metallic or a non-metallic material.

The reinforcing tether member preferably supports the tensile load applied to the shaft during use in the patient to thereby enhance the tensile strength of the catheter, and preferably tethers the tip to the catheter. Thus, the tether member preferably prevents the catheter polymeric tube from stretching and tearing. As a result, a catheter failure in which the catheter polymeric tubing tears under a tensile load is prevented or inhibited, and the risk of having the catheter distal tip detach from the catheter in the patient's body lumen is avoided. The tether member is configured to securely attach to the catheter tip, but without disadvantageously increasing bending stiffness. Distal tip bending stiffness must be sufficiently low to facilitate advancing the catheter to a desired location within the patient's often tortuous anatomy. Moreover, catheter manufacturability issues, such as the ability to locally change the diameter of the distal end of the catheter polymeric tubing having the tether member secured thereto, are preferably not disadvantageously affected by the tether member.

In some embodiments, the tether member is configured to provide one or more radiopaque markers, for example indicating generally the location of the distal end of the stent holder region of the catheter, or the distal end of the catheter.

Due to the reinforcing tether member of the invention, a stent delivery catheter system is provided with an improved combination of tensile strength, flexibility, and low profile, for improved ability to advance or retract the catheter in the patient's vasculature. The reinforcing tether member enhances the catheter tensile strength along at least a distal section of the catheter, and thereby prevents or inhibits the distal tip of the catheter from becoming dislocated from the catheter during use in a patient's body lumen. Additionally, the manufacturability of the catheter is preferably not disadvantageously affected by the tether member. These and other advantages of the invention will become more apparent from the following Detailed Description and accompanying exemplary drawings.

DETAILED DESCRIPTION OF THE PREFERRED EMBODIMENTS

Figure 1:
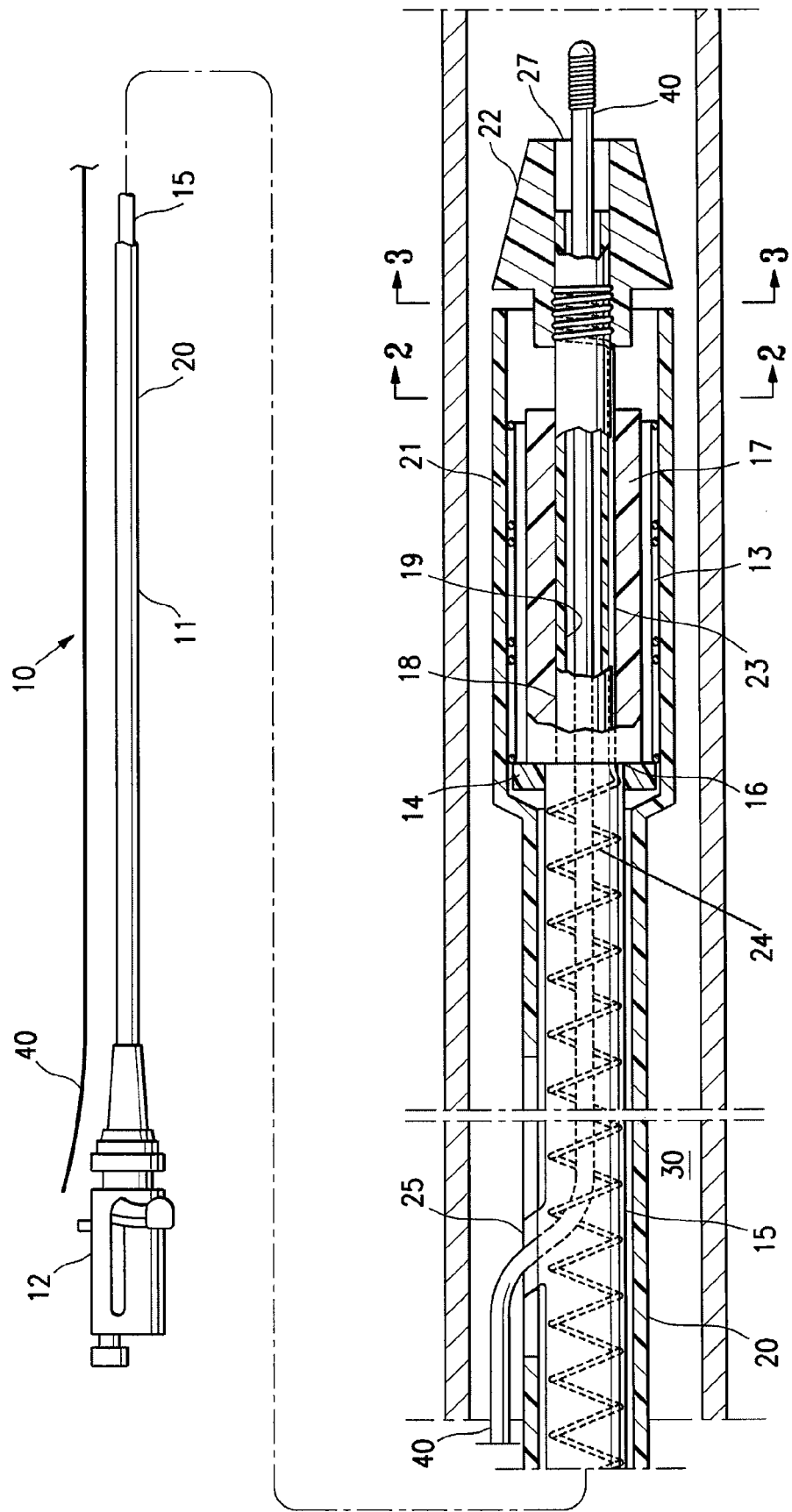
FIG. 1 is an elevational view, partially in section, of a stent delivery catheter system embodying features of the invention.

FIG. 1 illustrates an elevational, partially in section, view of a stent delivery catheter system 10 embodying features of the invention, generally comprising an elongated catheter 11 having a control handle assembly 12 attached to the proximal end of the catheter, and a stent 13 which is in a distal section of the catheter and which is configured to be implanted in a patient's body lumen 30. The illustrated embodiment is configured for delivering and deploying the stent in a patient's carotid artery. However, a catheter system of the invention could be used in a variety of body lumens, including coronary and peripheral vessels and non-vascular body lumens.

Figure 4:
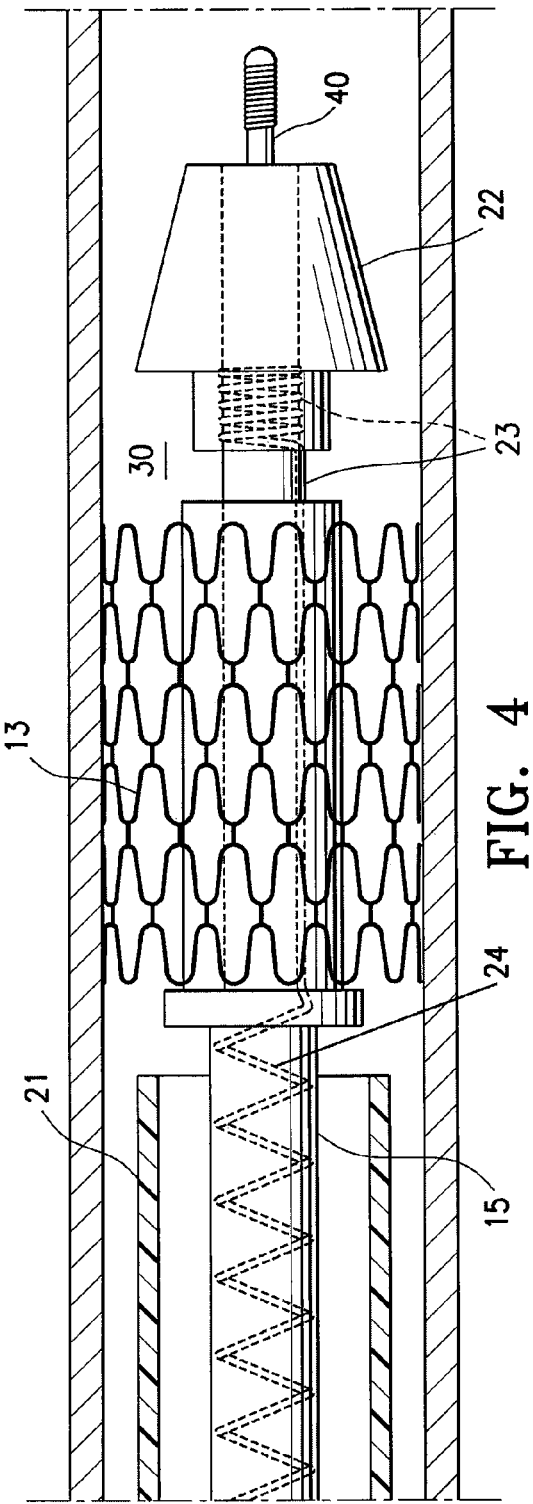
FIG. 4 illustrates the distal end section of the catheter system of FIG. 1, with the catheter outer tubular member in the retracted configuration and the stent expanded in the patient's body lumen.

The elongated catheter 11 generally comprises an inner tubular member 15, a stent holder region 17, a tubular member 18 defining a guidewire lumen 19 extending within at least a distal section of the inner tubular member 15, a distal tip 22 at a distal end of the guidewire lumen-defining tubular member 18, an outer tubular member 20 which has a stent restraining region 21 and which is adapted for axial movement with respect to the inner tubular member 15, and a reinforcing tether member 23 secured to the distal tip 22 of the inner tubular member 15. In the illustrated embodiment, the stent holder region 17 is a polymeric tube on, and typically secured to, an underlying distal section of the guidewire lumen-defining tubular member 18, and extending from a distal end 16 of the inner tubular member 15 (with a proximal end bonded to the distal end of a proximally adjacent section of the inner tubular member 15). A stent stop 14, formed for example of an annular member extending around the circumference of the inner tubular member 15/guidewire lumen-defining tubular member 18, has an outer diameter sized to interfere with proximal movement of the stent 13 to provide for accurate deployment of the stent 13 in the patient's body lumen 30. In the illustrated embodiment, the stent stop 14 is on an outer surface of the inner tubular member 15, such that the distal end 16 of the inner tubular member 15 extends at least to the stent stop, and typically slightly distal thereto. The proximal ends of the inner and outer tubular members are connected to the proximal handle 12, typically with the outer tubular member operatively connected to a mechanism such that operation of the handle mechanism causes the outer tubular member to move axially as the inner tubular member is held in place during stent deployment. Although not illustrated, an outer-most tubular member may be provided on a proximal end section of the outer tubular member 20 to provide additional stabilization. A variety of suitable handles can be used with a catheter of the invention, generally having a thumb wheel or slide activated mechanism. Fittings such as luer fittings are typically provided at the proximal end of the catheter for making a fluid connection to an inner lumen of the catheter. FIG. 1 illustrates the catheter with the stent 13 in a collapsed configuration releasably constrained within the outer tubular member region 21, for introduction and advancement of the catheter system 11 to a desired treatment location in the patient's body lumen 30. The catheter system 11 is typically advanced with a guidewire 40 slidably disposed in the guidewire lumen 19 to position the stent at the desired treatment location, and the outer tubular member 20 is then proximally retracted to cause the stent to radially expand away from the outer surface of the inner tubular stent holder region tube 17 in the body lumen 30, and the catheter 11 proximally withdrawn, leaving the stent 13 implanted in the body lumen 30. FIG. 4 illustrates the outer tubular member proximally retracted and the stent 13 radially expanded against the wall of the body lumen 30.

The inner tubular member 15 and outer tubular member 20 extend to the catheter 11 proximal end, and although the inner and outer tubular members 15, 20 are each illustrated as a single extrusion in FIG. 1, it should be understood that they may have multiple layers or sections. For example, the inner tubular member is preferably formed of multiple tubes joined end to end, typically providing flexibility transitions axially, such as a high strength (e.g., metallic) proximal tubular member with a proximal end secured to a distal end of a more flexible distal polymeric tubular member. In the embodiment of FIG. 1, the inner tubular member 15 has a coil layer 24 in the polymeric tubular member at least along a section thereof. The coil 24 (shown in dashed line within the polymeric wall of the inner tubular member 15 in FIG. 1) is typically a metallic round wire, although it may alternatively be a flat ribbon or a braided layer, configured to reinforce the inner tubular member (e.g., for enhanced axial compression strength). Similarly, the tubular member 18, configured to slidably receive guidewire 40 therein, in a presently preferred embodiment is formed of a multilayer extrusion having an inner lubricious layer to facilitate guidewire movement therein and one or more different outer polymeric layers, and is most preferably a trilayer extrusion. The materials and dimensions of the polymeric tubular member 18 are configured to provide a tubular member that is flexible, lubricious (inner layer), and heat bondable (outer layer) to adjacent polymeric components of the catheter 11. The trilayer tubular member 18 is typically formed by coextrusion, followed by post extrusion dimensional processing such as flaring or necking an end of the extruded tubular member to a desired size. The guidewire lumen-defining tubular member 18 extends proximally to a guidewire proximal port 25. In the illustrated embodiment, the guidewire proximal port 25 is distally spaced from the catheter proximal end, such that the catheter is configured for rapid exchange. The area of the shaft of the catheter 11 forming the rapid exchange port 25, typically referred to as the rapid exchange notch, can be formed using a variety of suitable designs, generally having the proximal end of the guidewire lumen-defining tubular member 18 fusion bonded to the surrounding surface of the inner tubular member 15 to sealingly form the opening in the shaft which defines the port 25 and provides access into the guidewire lumen 19. A break or slot 26 in the wall of the outer tubular member 20 allows the outer tubular member to be proximally retracted with the guidewire 40 extending out the port 25, and an orientation mechanism may be provided as is conventionally known, which allows for relative axial movement between inner and outer tubular members 15, 20 while maintaining the guidewire proximal port 25 rotationally oriented at the slot 26. The guidewire lumen-defining tubular member 18 is typically fusion bonded to the inner tubular member 15 at least at the proximal guidewire port 25.

In the illustrated embodiment, the distal tip 22 is a distal tip member with an inner surface secured to an outer surface of a distal end of the guidewire lumen-defining tubular member 18. However, in an alternative embodiment (not shown), the distal tip is formed as an integral, one-piece unit with the guidewire lumen-defining tubular member 18. The distal tip member 22 in the illustrated embodiment has a proximal stem section, and a radially enlarged (maximum outer diameter) section with a tapering outer surface which is substantially flush with the distal end of the outer tubular member stent restraining region 21 to facilitate maneuvering the catheter through the patient's tortuous anatomy. A small gap is illustrated between the distal end of the outer tubular member stent restraining region 21 and the proximal end of the maximum outer diameter portion of the distal tip member 22 in FIG. 1, although it should be understood that the distal end of the outer tubular member stent restraining region 21 could be configured to be located closer to or further from the distal tip in the advanced configuration as desired. The distal tip member 22 is typically formed of a relatively soft polymeric material having a lower Shore durometer hardness than at least a layer of the guidewire lumen-defining tubular member 18 proximally adjacent thereto. In one embodiment, the distal tip member is formed of a blend of polymeric material and radiopaque material, such that it is radiopaque.

The distal tip member 22 is typically heat fusion bonded to the outer surface of the guidewire lumen-defining tubular member 18. Adhesive bonding is a less preferred option, at least in part due to issues relating to reliability, manufacturability, and stiffness at the distal end of the catheter. In a presently preferred embodiment, the bond between the distal tip member 22 and tubular member 18 extends along the proximal stem section of the distal tip and not along the larger diameter tapering section of the distal tip. The bond strength along the bond between the distal tip member 22 and tubular member 18 is sufficiently strong to withstand the force applied thereto during use of the catheter in the patient's body lumen. The distal end of the guidewire lumen-defining tubular member 18, located within the distal tip member 22 lumen, is proximally spaced from the distal end of the distal tip member 22 in the embodiment of FIG. 1. Specifically, it is closer to the distal end than to the proximal end of the distal tip member 22 to facilitate backloading of the guidewire into the catheter, although it could alternatively be at other locations along the length of the distal tip member. A distal end of the guidewire lumen 19 and a guidewire distal port 27 at the distal end of the catheter 11 are defined by the distal end of the distal tip member 22 in the illustrated embodiment.

Figure 3:
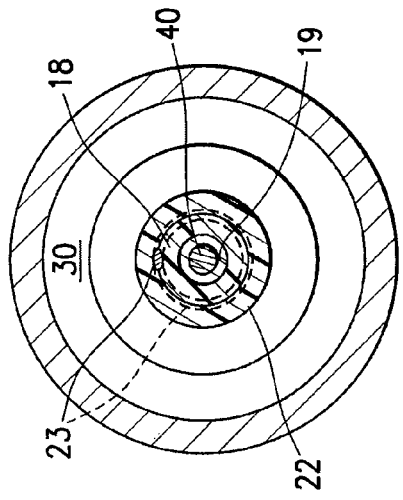
FIG. 3 is a transverse cross sectional view of the catheter system of FIG. 1, taken along line 3-3.
Figure 2:
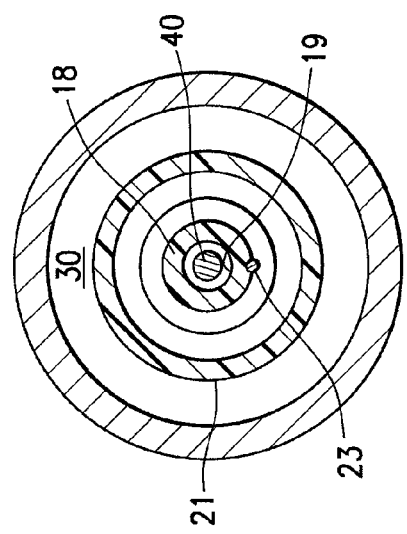
FIG. 2 is a transverse cross sectional view of the catheter system of FIG. 1, taken along line 2-2.

The tether member 23, which extends between the distal tip member 22 and the inner tubular member 15 along the guidewire lumen-defining tubular member 18, is configured to enhance the tensile strength of the catheter. The tether member 23 prevents or inhibits a catheter failure in which a section of the guidewire lumen-defining tubular member 18 located proximal to the distal tip 22 could partially or fully tear under a tensile load applied during use of the catheter within the patient's body lumen. In the embodiment of FIG. 1, the tether member 23 is a round wire, as best shown in FIGS. 2 and 3 illustrating transverse cross sections of FIG. 1, taken along lines 2-2 and 3-3, respectively. However, the tether member 23 could alternatively be a flat ribbon. The tether member 23 extends in the distal tip member 22 at least in part helically, and extends axially from the proximal end of the distal tip member 22 on the guidewire-defining tubular member 18. Specifically, in the embodiment of FIG. 1, the tether member extends in an axial manner distally from the distal end of the coil 24 of the inner tubular member 15. The tether member extending from the coil 24 is typically an integral, one-piece extension of the wire forming the coil 24, although it can alternatively be connected to the distal end of the coil 24, for example by soldering to fixedly bond it thereto. The tether member 23 extends axially along the entire section of the tubular member 18 located between the distal end of the coil 24 reinforced section of the inner member 15 and the distal tip member 22. The terminology "helically" as used herein should be understood to refer generally to a spiraling, coil or spring-like configuration, as opposed to a substantially axially aligned section of the tether member which extends substantially straight (i.e., with no intentionally induced spiraling or curving around the tubular member 18).

The tether member 23 is typically formed of a metallic material such as stainless steel, although high strength non-metallic materials such as a graphite or KEVLAR fiber can be used, providing a high tensile strength but small diameter member. The axially extending section of the tether member 23 does not reinforce the catheter (i.e., the guidewire lumen-defining tubular member 18 on which it extends) in the radial direction, unlike a coiled or braided reinforcing layer, and as a result does not prevent or inhibit locally changing the diameter of the end of the tubular member 18 extrusion (i.e., flaring) during the manufacturing of the catheter. Additionally, unlike a reinforcer which spirals around a catheter shaft tubular member, the axially extending section of the tether member of the invention has no tendency to straighten under tension, and thus is configured to provide the required tensile strength. For example, in one embodiment, a stainless steel 0.004 inch diameter round wire or a 0.002×0.006 inch ribbon tether member provides about 4 lbs of strength.

In one embodiment, the tether member 23 is adhered to at least a section of the outer surface of the guidewire lumen-defining tubular member 18 by melting the surrounding polymer so that the tether member becomes at least partially embedded in the tubular member 18 outer surface (see, e.g., FIG. 2). In the embodiment in which the tether member is formed by an extension of the inner tubular member coil 24, the tether member is preferably adhered to the tubular member 18 in post-extrusion processing, whereas a tether member formed by a separate length of wire or ribbon bonded to the distal end of the coil 24 can alternatively be adhered during extrusion of the tubular member 18. Although the tether member is embedded in the tubular member 18 at the location of transverse cross section line 2-2 in the embodiment of FIG. 1, it should be understood that the tether member is not necessarily embedded along its entire length, and may alternatively be secured to the catheter at both ends of the tether member with at least a portion of an intermediate section of the tether member therebetween being unsecured. In one embodiment, the tether member is secured to the catheter at both ends of the tether member and at one or more portions along an intermediate section therebetween, such that the tether member 23 has one or more unsecured intermediate portions located between the secured end sections. The tether member 23 can be adhered to the tubular member 18 by sandwiching under an outer layer, e.g., a heat shrink outer layer (not shown) or the stent holder region tube 17. In the embodiment illustrated in FIG. 1, the tether member 23 is partially embedded in the outer surface of the tubular member 18 and in the inner surface of the distal tip member 22, as best shown in FIG. 3, although it could alternatively be embedded to a greater or lesser extent, or not at all. One embodiment of assembling the catheter 11 of FIG. 1 involves first bonding the tether wire to the inner member coil 24 (in an embodiment in which the tether member is not an integral extension of the coil), inserting the guidewire lumen-defining tubular member 18 into the inner tubular member 15, applying heat and pressure at various parts of the guidewire lumen-defining tubular member 18 to embed the tether wire into the outer surface of the tubular member 18, attaching the stent holder tube 17 and stent stop 14 to the inner member assembly, inserting the distal end of the guidewire lumen-defining tubular member 18 (with tether wire 23 thereon) into the proximal end of the distal tip member 22, applying heat and pressure to the distal tip member 22 to adhere the guidewire lumen-defining tubular member 18 to the distal tip member 22 and embed the tether wire 23, and inserting the assembly into the outer tubular member 20 to constrain the stent 13. In the illustrated embodiment, the stent 13 surrounds but is not mounted onto (crimped onto) the outer surface of the stent holder region tube 17, although in alternative suitable stent delivery system designs it is carried in the collapsed configuration on the outer surface of the stent holder region tube 17.

Figure 5:
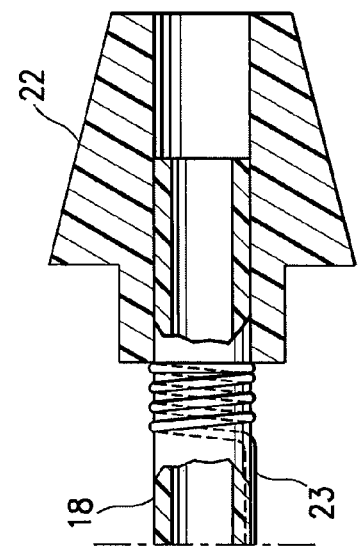
FIG. 5 illustrates an alternative embodiment of the tether member configuration in the distal tip member, in which the tether member has a proximal axially extending portion in the distal tip member and a distal coiled portion at the distal end of the distal tip member.

The tether member 23 has a helically coiled section in the distal tip member 22 (for ease of illustration, the tether member 23 is shown in an elevational view, not in longitudinal cross section, in FIG. 1). Specifically, in the embodiment of FIG. 1, the tether member 23 distal end is in a proximal stem section of the distal tip member proximally spaced from a tapered distal section of the distal tip member, and the reinforcing tether member 23 extends helically in the proximal section of the distal tip member with a relatively tight coil winding configured to provide a radiopaque marker (i.e., appear with sufficient brightness to be clearly visible under fluoroscopy at typical settings). The radiopaque marker provided by the coiled section of the tether wire 23 in the embodiment of FIG. 1 is particularly useful to indicate the distal end of the stent 13/stent holder region 17 during positioning of the catheter system at a treatment site in the patient's body lumen 30. FIG. 5 illustrates an alternative embodiment in which the reinforcing tether member 23 extends substantially the entire length of the distal tip member 22, and has a first portion within the distal tip member along which the reinforcing tether member extends axially, and a second portion within the distal tip member, distal to the first portion, along which the reinforcing tether member extends helically. The relatively tight coil winding, e.g., with a pitch or interturn distance of about 0.2 mm to about 0.4 mm for a 0.1 mm diameter wire, is typically selected to balance factors such as those affecting adhesion strength, flexibility and radiopacity, and in a presently preferred embodiment is not a stacked (touching coil turns) coil. The radiopaque marker provided by the coiled section of the tether wire in the embodiment of FIG. 5 is particularly useful to indicate the distal end of the catheter relative to an embolic protection device (not shown), commonly used in carotid stenting procedures to trap or filter any debris in the body lumen 30 distal to the catheter 11 as is conventionally known for carotid stenting. Such embolic protection devices are configured to be slidably received in the guidewire lumen 19 of the catheter 11, such that the terminology "guidewire lumen" as used herein in relation to a catheter of the invention should be understood to refer to a lumen generally configured to slidingly receive a device such as a guidewire or other device therein, and particularly the wire-like body of a guidewire or embolic protection device. The relatively tight coil winding providing a marker at a specific location in the tip is useful with a distal tip member 22 which is nonradiopaque or which is itself radiopaque (e.g., formed of a polymer/radiopaque particle blend).

Figure 6:
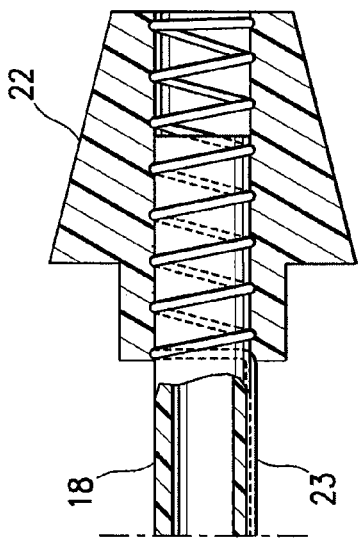
FIG. 6 illustrates an alternative embodiment of the tether member configuration in the distal tip member, in which the tether member is loosely coiled throughout the length of the distal tip member.

FIG. 6 illustrated an alternative embodiment in which the reinforcing tether member 23 extends helically in the distal tip member 22 with a relatively loose coil spacing throughout the length in the distal tip member. The relatively loose coil spacing, e.g., with a pitch or interturn distance of about 0.5 mm to about 1 mm for a 0.1 mm diameter wire, does not appear at typical settings on the fluoroscope and thus does not function as a radiaopaque marker. However, the relatively loose coil spacing provides improved adhesion securing the tether member 23 to the distal tip member 22, and is thus preferred in embodiments in which a radiopaque marker provided by the tether member is not required at the distal end of the stent/catheter. The tether member in the distal tip can have a variety of suitable configurations provided that suitable adhesion strength is obtained, and including having a variable winding pitch or having multiple relatively tightly wound coiled sections so long as the resulting radiopaque appearance is not undesirable.

The tether member 23 is typically secured to the distal tip member 22 by placing the coiled section of the tether member 23 supported on a mandrel within the distal tip member lumen, and applying heat and/or pressure on the outer surface of the distal tip member 22 to cause the tether member to embed into the polymeric material defining the inner lumen of the distal tip member and thereby become fixedly adhered thereto. The tether member 23 is preferably embedded in the inner surface of the distal tip member 22 such that it does not interfere with guidewire movement within the distal tip member 22, although it is not necessarily completely encased within the polymeric material of the distal tip member (i.e., the inner surface of the tether member can be exposed or protrude slightly radially inwardly from the inner surface of the distal tip member 22).

Figure 7:
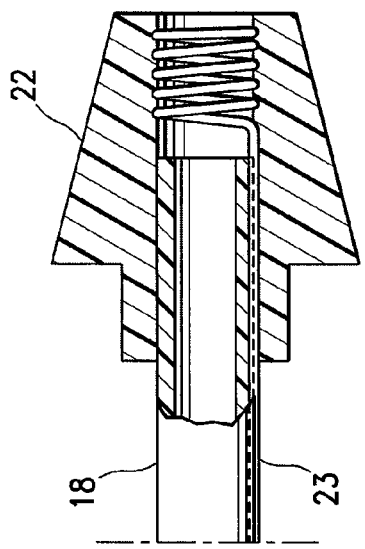
FIG. 7 illustrates an alternative embodiment of the tether member, in which the tether member extends helically proximally adjacent to the proximal end of the distal tip.

FIG. 7 illustrates an alternative embodiment in which the reinforcing tether member 23 extends helically proximally adjacent to the proximal end of the distal tip member 22. Preferably, the tether member 23 extends helically with a relatively tight coil winding configured to provide a radiopaque marker as discussed above, which generally indicates the distal end of the stent under fluoroscopy. In the illustrated embodiment, the distal end of the tether member abuts the proximal end of the distal tip member 22 and may be bonded thereto. The tether member 23 of the embodiment of FIG. 7 extends axially along the guidewire lumen-defining tubular member 18 from the proximal end of the helically extending section as discussed above, and is typically secured to the inner tubular member. For example, in one embodiment, the tether member 23 of FIG. 7 is an integral or bonded extension of the inner tubular member reinforcing member as discussed in the embodiment of FIG. 1. Similar to the embodiment of FIG. 1, the tether member 23 of the embodiment of FIG. 7 may be a round wire or flat ribbon.

Figure 8:
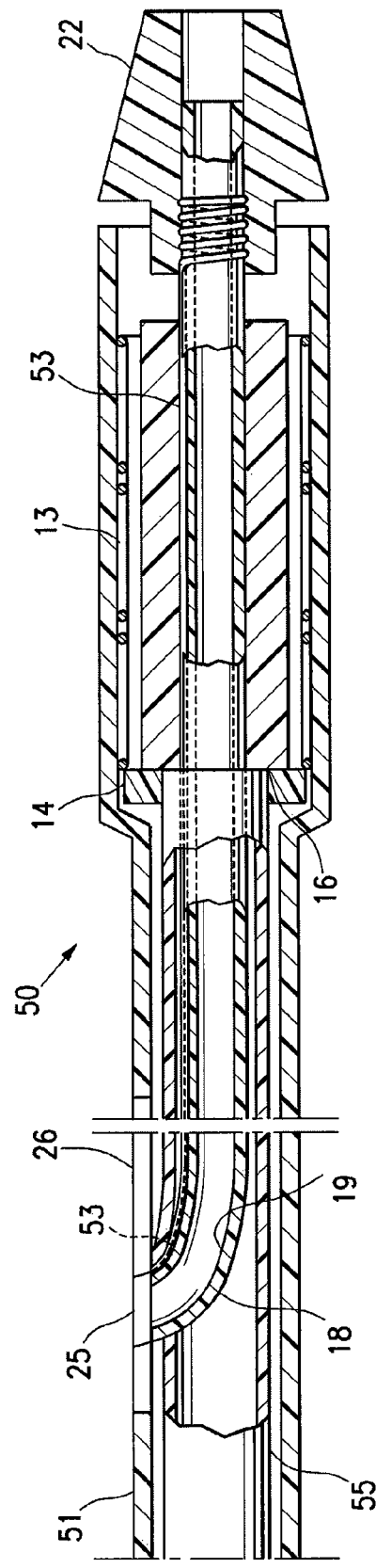
FIG. 8 is an elevational view, partially in section, of a distal section of an alternative embodiment of the stent delivery catheter system, having a reinforcing tether member extending axially on the guidewire lumen-defining tubular member from the guidewire proximal port to the proximal end of the distal tip member.

FIG. 8 illustrates a distal section of an alternative stent delivery catheter system 50 embodying features of the invention, in which the catheter 51 has an inner tubular member 55 that is not coil supported (at least along the distal section thereof adjacent to the guidewire lumen-defining tubular member 18). In the embodiment of FIG. 8, the tether member 53 extends to a proximal end section of the tubular member 18 at the guidewire proximal port 25, where the inner tubular member 55 is fused to the tubular member 18. The tether member 23 is thus between the inner tubular member 55 and the tubular member 18 from the port 25 to the distal end 16 of the inner tubular member 55 and thereafter extends to the distal tip as in the embodiment of FIG. 1. The tether member 53 is therefore positioned between the inner tubular member 55 and underlying section of the guidewire lumen-defining tubular member 18 before the rapid exchange notch is formed, and fusing the inner member 55 to the tubular member 18 to form the notch securely bonds the proximal end of the tether member 53 to the catheter 51. The tether member 53 may be secured to the guidewire lumen-defining tubular member 18 along all or nearly all of the length of the tubular member 18, or at end sections so that there is at least one intermediate unsecured portion of the tether member 53. In a presently preferred embodiment, the tether member is secured to the catheter at both ends and at one or more portions along the intermediate section, such that the tether member has intermediate unsecured portion(s) located between secured end sections of the reinforcing tether member (which may be separated by intermediate intermittent secured portions which are secured to the guidewire lumen-defining tubular member). In the illustrated embodiment, the inner tubular member 55, at least along a distal section, is a polymeric tube. Similar to the coil supported inner tubular member 15 of FIG. 1, the inner tubular member 55 of FIG. 8 may have a high strength proximal section formed for example by a metallic tube (not shown) with a distal end bonded to the distal section polymeric tube. Although not illustrated, the distal end 16 of the inner tubular member 55 in the embodiment of FIG. 8 may have a tapered or wedge shape providing a gradual distally decreasing stiffness therealong.

The tether member 23/53 is typically a relatively small diameter wire which in one embodiment has an outer diameter of about 0.5 mm to about 0.15 mm. The tether member is particularly useful in low profile catheters having relatively thin walled, small sized guidewire lumens, e.g., relatively small sized catheter systems configured for use with a guidewire of 0.018 inches or less, and most preferably with a 0.014 inch guidewire.

It should be understood that the reinforcing tether member 23/53 of the invention can be used in a variety of suitable catheter designs, generally including an inner (e.g., guidewire) lumen-defining tubular member extending to a distal tip. For example, although the stent delivery system has a self-expanding stent, a catheter of the invention can alternative be configured to deploy a non-self expanding stent requiring a radially expansive force, applied as by inflation of a balloon, to deploy the stent. Additionally, although illustrated as a rapid exchange catheter with a guidewire proximal port distally spaced from the catheter proximal end, the catheter could alternatively have a full length guidewire lumen extending to the proximal end of the catheter. Similarly, although illustrated with inner tubular members 15/55, a variety of suitable catheter shaft designs can be used with a variety of suitable inner members generally extending within and adapted for axial movement relative to the outer tubular member 20.

The catheter components such as the inner and outer tubular members 15/55, 20 and guidewire lumen-defining tubular member 18, can be formed of materials found useful in catheter construction. For example, the polymeric tubular members can be formed of materials such as polyamides (e.g., nylon), polyamide copolymers (e.g., polyether block amide), polyolefins (e.g., polyethylene), polyurethanes, polyesters, and the like. Generally speaking, the more proximal portions of the catheter inner and outer tubular members will be stiffer than the distal portions, to provide the catheter sufficient pushability, and the catheter distal section is configured to provide flexibility and trackability to advance through the patient's vascular system by tracking on a wire in the lumen 19.

While described herein in terms of certain preferred embodiments, various modifications and improvements can be made to the invention without departing from the scope thereof. For example, a variety of suitable proximal sections of the tether member, extending in a proximal section of the catheter, can be used with a tether member of the invention. For example, a mandrel or core wire of the catheter which generally forms an inner member of the catheter and which extends distally from the proximal end of the catheter can be adapted at its distal end section to form the tether member of the invention. Additionally, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

We claim:

1. A stent delivery catheter system, comprising
a) an elongated delivery catheter having an inner tubular member, a stent holder region, a guidewire lumen-defining tubular member extending within at least a distal section of the inner tubular member, a distal tip at a distal end of the guidewire lumen-defining tubular member, an outer tubular member which has a stent restraining region and which is adapted for axial movement with respect to the stent holder region to transition from an advanced configuration surrounding the stent holder region to a proximally retracted configuration, and having a reinforcing tether member secured to the inner tubular member, which has a distal end length extending helically in the distal tip member or proximally adjacent to the proximal end of the distal tip member, and a substantially axially aligned section which extends substantially straight from the proximal end of the helical end length and through the stent holder region such that the tether member is configured to enhance the tensile strength of the catheter; and
b) a self-expanding stent which is in a collapsed configuration surrounding the stent holder region of the catheter with the catheter outer tubular member in the advanced configuration, and which is configured to be deployed by radially self-expanding from the collapsed configuration upon movement of the catheter outer tubular member to the retracted configuration.

2. The catheter system of claim 1 wherein the reinforcing tether member is a wire or ribbon formed of a metallic material or a high strength non-metallic material.

3. The catheter system of claim 1 wherein the inner tubular member has a coil or braided reinforcing member embedded therein, and the reinforcing tether member is an integral extension of, or is bonded to, the reinforcing member.

4. A stent delivery catheter system, comprising
a) an elongated delivery catheter having an inner tubular member, a stent holder region, a guidewire lumen-defining tubular member extending within at least a distal section of the inner tubular member, a distal tip at a distal end of the guidewire lumen-defining tubular member, an outer tubular member which has a stent restraining region and which is adapted for axial movement with respect to the stent holder region to transition from an advanced configuration surrounding the stent holder region to a proximally retracted configuration, and having a reinforcing tether member secured to the distal tip member and secured to the inner tubular member, which extends at least in part helically in the distal tip member, and includes a substantially axially aligned section which extends substantially straight from the proximal end of the distal tip member on the guidewire lumen-defining tubular member and through the stent holder region such that the tether member is configured to enhance the tensile strength of the catheter; and
b) a self-expanding stent which is in a collapsed configuration surrounding the stent holder region of the catheter with the catheter outer tubular member in the advanced configuration, and which is configured to be deployed by radially self-expanding from the collapsed configuration upon movement of the catheter outer tubular member to the retracted configuration.

5. The catheter system of claim 1 wherein the distal tip is a distal tip member with a surface bonded to a distal end section of the guidewire lumen-defining tubular member.

6. The catheter system of claim 5 wherein the distal tip member is formed of a polymeric material having a lower Shore durometer hardness than at least a layer of the guidewire lumen-defining tubular member secured thereto.

7. The catheter system of claim 5 wherein the distal tip member is formed of a blend of polymeric material and radiopaque material, such that it is radiopaque.

8. The catheter system of claim 5 wherein the reinforcing tether member distal end is located in a proximal section of the distal tip member proximally spaced from a tapered distal section of the distal tip member.

9. The catheter system of claim 8 wherein the reinforcing tether member extends helically in the proximal section of the distal tip member with a coil spacing configured to provide a radiopaque marker.

10. The catheter system of claim 5 wherein the reinforcing tether member extends substantially the entire length of the distal tip member.

11. The catheter system of claim 8 wherein the reinforcing tether member extends helically in the distal tip member with a coil spacing throughout the length in the distal tip member.

12. The catheter system of claim 8 wherein the reinforcing tether member has a first portion within the distal tip member along which the reinforcing tether member extends axially, and a second portion within the distal tip member, distal to the first portion, along which the reinforcing tether member extends helically.

13. The catheter system of claim 1 wherein the guidewire lumen-defining tubular member has a rapid-exchange guidewire proximal port distally spaced from a proximal end of the catheter.

14. The catheter system of claim 13 wherein the reinforcing tether member is embedded in an outer surface of the guidewire lumen-defining tubular member along substantially the entire length of the guidewire lumen-defining tubular member from the guidewire proximal port to the distal tip member.

15. The catheter system of claim 13 wherein the reinforcing tether member is secured to the guidewire lumen-defining tubular member at the guidewire proximal port.

16. The catheter system of claim 1 including an outer covering sleeve heat shrunk onto the guidewire lumen-defining tubular member and reinforcing tether member thereon.

17. The catheter system of claim 1 wherein the reinforcing tether member has at least one intermediate unsecured section which is between bonded end sections of the reinforcing tether member and along which the reinforcing tether member is not bonded to the catheter.

18. The catheter system of claim 1 wherein the distal tip has a radially enlarged section having an outer diameter substantially equal to an outer diameter of a distal end of the outer tubular member stent restraining region, and larger than a proximally adjacent stem section of the distal tip and a proximally adjacent section of the catheter inner tubular member, and the tether member distal end is in the stem section of the distal tip proximal to a distal end of the guidewire lumen-defining tubular member in the distal tip.

19. A stent delivery catheter system, comprising
a) an elongated delivery catheter having an inner member, a stent holder region, a guidewire lumen-defining tubular member extending within the stent holder region, a distal tip at a distal end of the guidewire lumen-defining tubular member, an outer tubular member which has a stent restraining region and which is adapted for axial movement with respect to the stent holder region to transition from an advanced configuration surrounding the stent holder region to a proximally retracted configuration, and having a reinforcing tether member which includes a substantially axially aligned section that extends substantially straight through the stent holder region and on at least a portion of the guidewire lumen-defining tubular member from a distal end of the inner tubular member to a proximal end of the distal tip member and which has an annular distal end extending around the circumference of the guidewire lumen-defining tubular member; and
b) a self-expanding stent which is in a collapsed configuration surrounding the stent holder region of the catheter with the catheter outer tubular member in the advanced configuration, and which is configured to be deployed by radially self-expanding from the collapsed configuration upon movement of the catheter outer tubular member to the retracted configuration.

20. The stent delivery catheter system of claim 19 wherein the inner tubular member has a coil or braided reinforcing member embedded therein, and the reinforcing tether member is an integral extension of, or is bonded to, the reinforcing member.

21. A stent delivery catheter system, comprising:
a) an elongated delivery catheter having an inner tubular member, a stent holder region, a guidewire lumen-defining tubular member extending within at least a distal section of the inner tubular member, a distal tip at a distal end of the guidewire lumen-defining tubular member, an outer tubular member which has a stent restraining region and which is adapted for axial movement with respect to the stent holder region to transition from an advanced configuration surrounding the stent holder region to a proximally retracted configuration, a reinforcing tether member secured to the inner tubular member, which has a distal end length extending helically in the distal tip member or proximally adjacent to the proximal end of the distal tip member, and which has a proximal portion that extends axially on the guidewire lumen-defining tubular member from the proximal end of the helical end length and includes a substantially axially aligned section that extends substantially straight through the stent holder region, the inner tubular member having a coil or braided reinforcing member embedded therein which extends proximal to the stent holder region, wherein the reinforcing tether member is an integral extension of, or is bonded to, the axial portion of reinforcing member; and b) a self-expanding stent which is in a collapsed configuration surrounding the stent holder region of the catheter with the catheter outer tubular member in the advanced configuration, and which is configured to be deployed by radially self-expanding from the collapsed configuration upon movement of the catheter outer tubular member to the retracted configuration.

22. The catheter system of claim 21 wherein the reinforcing tether member is a wire or ribbon formed of a metallic material or a high strength non-metallic material.

23. The catheter system of claim 21 wherein the reinforcing tether member is embedded in an outer surface of the guidewire lumen-defining tubular member along substantially the entire length of the guidewire lumen-defining tubular member from the proximal end of the stent holder region to the distal tip member.

24. The catheter system of claim 21 wherein the guidewire lumen-defining tubular member has a rapid-exchange guidewire proximal port distally spaced from a proximal end of the catheter.

* * * * *